US009012402B1

(12) United States Patent
Blanchard

(10) Patent No.: US 9,012,402 B1
(45) Date of Patent: Apr. 21, 2015

(54) GEL FOR TOPICAL DELIVERY OF NSAIDS TO PROVIDE RELIEF OF MUSCULOSKELETAL PAIN AND METHODS FOR ITS PREPARATION

(71) Applicant: James Blanchard, Tucson, AZ (US)

(72) Inventor: James Blanchard, Tucson, AZ (US)

( * ) Notice: Subject to any disclaimer, the term of this patent is extended or adjusted under 35 U.S.C. 154(b) by 0 days.

(21) Appl. No.: 14/302,164

(22) Filed: Jun. 11, 2014

(51) Int. Cl.
*A61K 31/192* (2006.01)
*A61K 9/00* (2006.01)
*A61K 45/06* (2006.01)
*A61K 47/10* (2006.01)

(52) U.S. Cl.
CPC ............ *A61K 9/0014* (2013.01); *A61K 31/192* (2013.01); *A61K 45/06* (2013.01); *A61K 47/10* (2013.01)

(58) Field of Classification Search
USPC .................................................. 514/557, 944
See application file for complete search history.

(56) References Cited

U.S. PATENT DOCUMENTS

| | | | |
|---|---|---|---|
| 4,188,373 A | 2/1980 | Krezanoski | 424/78 |
| 4,393,076 A | 7/1983 | Noda et al. | 424/317 |
| 4,474,751 A | 10/1984 | Haslam et al. | 514/2.4 |
| 4,474,753 A | 10/1984 | Haslam et al. | 424/78 |
| 4,478,822 A | 10/1984 | Haslam et al. | 424/78 |
| 4,511,563 A | 4/1985 | Schmolka | 514/162 |
| 4,534,980 A | 8/1985 | Itoh et al. | 514/570 |
| 4,767,619 A | 8/1988 | Murray | 424/78 |
| 4,861,760 A | 8/1989 | Mazuel et al. | 514/54 |
| 4,883,660 A | 11/1989 | Blackman et al. | 424/78 |
| 4,999,379 A | 3/1991 | Fankhauser | 516/567 |
| 5,093,133 A | 3/1992 | Wisniewski et al. | 424/484 |
| 5,318,780 A | 6/1994 | Viegas et al. | 424/427 |
| 5,374,661 A | 12/1994 | Betlach, II | 514/772.4 |
| 5,614,171 A | 3/1997 | Clavenna et al. | 424/45 |
| 5,618,516 A | 4/1997 | Clavenna et al. | 424/45 |
| 5,654,337 A | 8/1997 | Roentsch et al. | 514/570 |
| 5,716,609 A | 2/1998 | Jain et al. | 424/78.05 |
| 5,837,289 A | 11/1998 | Grasela et al. | 424/484 |
| 5,863,560 A | 1/1999 | Osborne | 424/484 |
| 5,897,880 A | 4/1999 | Drizen et al. | 424/484 |
| 5,976,566 A | 11/1999 | Samour et al. | 424/449 |
| 6,060,085 A | 5/2000 | Osborne | 424/484 |
| 6,083,996 A | 7/2000 | Büyüktimkin et al. | 514/772.6 |
| 6,277,892 B1 | 8/2001 | Deckner et al. | 514/772.4 |
| 6,368,618 B1 | 4/2002 | Jun et al. | 424/449 |
| 6,399,093 B1 | 6/2002 | Petrus | 424/448 |
| 6,420,394 B1 | 7/2002 | Supersaxo | 514/338 |
| 6,635,674 B1 | 10/2003 | Kaneko et al. | 514/562 |
| 6,638,981 B2 | 10/2003 | Williams et al. | 514/656 |
| 6,645,520 B2 | 11/2003 | Hsu et al. | 424/449 |
| 6,723,345 B2 | 4/2004 | Drizen et al. | 424/484 |
| 6,835,392 B2 | 12/2004 | Hsu et al. | 424/449 |
| 7,138,394 B2 | 11/2006 | Schwarz et al. | 514/226.5 |
| 7,473,432 B2 | 1/2009 | Cevc et al. | 424/450 |
| 7,666,914 B2 * | 2/2010 | Richlin et al. | 514/23 |
| 8,470,886 B2 | 6/2013 | King-Smith et al. | 514/570 |
| 8,541,470 B2 | 9/2013 | Davis | 514/567 |
| 2001/0012849 A1 | 8/2001 | Wechter | 514/330 |
| 2004/0071767 A1 | 4/2004 | Cevc et al. | 424/450 |
| 2005/0042241 A1 | 2/2005 | Cusic et al. | 424/401 |
| 2005/0096371 A1 | 5/2005 | Krishnan et al. | 514/406 |
| 2005/0158348 A1 | 7/2005 | Schwarz et al. | 424/400 |
| 2006/0241175 A1 | 10/2006 | Schwarz et al. | 514/458 |
| 2007/0141182 A1 | 6/2007 | Niazi | 424/755 |
| 2009/0053290 A1 | 2/2009 | Sand et al. | 424/449 |
| 2009/0060990 A1 | 3/2009 | Cevc et al. | 424/450 |
| 2009/0062244 A1 | 3/2009 | Schwarz et al. | 514/170 |
| 2010/0099767 A1 * | 4/2010 | Davis | 514/567 |

FOREIGN PATENT DOCUMENTS

| | | | | |
|---|---|---|---|---|
| WO | WO9749405 | 12/1997 | ............ | A61K 31/52 |
| WO | WO0051575 | 9/2000 | ............ | A61K 9/70 |
| WO | WO2005009510 | 2/2005 | | |
| WO | WO2007103555 | 9/2007 | ............ | A61K 8/49 |
| WO | WO2008049020 | 4/2008 | ............ | A61K 9/00 |
| WO | WO2012087749 | 6/2012 | ............ | A61F 13/00 |

OTHER PUBLICATIONS

Aberle, T. and Burchard, W. (1997), Starches in Semidilute Aqueous Solution. Starch/Stärke, 49: 215-224. doi: 10.1002/star.19970490602.
Airaksinen, O., Venalainen, J., Piletilainen, T., Ketoprofen 2.5% gel versus placebo gel in the treatment of acute soft tissue injuries. Int. J. Clin. Pharm. Therapy and Tox. 31: 561-563 (1993).
Altman, R.D., Barthel, H.R., Topical therapies for osteoarthritis, Drugs 71:1259-1279 (2011).
American College of Rheumatology Offers Guidance for Assessing Arthritis Pain Medication Usage, Press Release, Amer. Coll. of Rheumatology, Dec. 22, 2004.
Anon, Carbopol® Ultrez 10 polymer for personal care applications, TDS-225, Lubrizol Advanced Materials, Inc., Cleveland, OH 44141, Jan. 2002.
Anon, Clinical knowledge summary for sprains and strains, National Institute for Health and Care Excellence (NICE), Oct. 2012.
Anon, Easing joint pain: Are NSAIDs right for you? Consumer Reports (2013) http://www.consumerreports.org/health/resources/pdf/best-buy-drugs/2pager_NSAIDs.pdf.
Anon, The pain management market outlook to 2016, Business Insights, 2011). http://www.futuramedical.com/content/products/pain_relief.asp.
Ballerini, R., Casini, A., Chinol, M., Mannucci, C., Giaccai, L., Salvi, M., Study on the absorption of ketoprofen topically administered in man: comparison between tissue and plasma levels, Int. J. Clin. Pharm. Res.VI: 69-72 (1986).

(Continued)

*Primary Examiner* — Rei-Tsang Shiao
(74) *Attorney, Agent, or Firm* — Hayes Soloway P.C.

(57) ABSTRACT

A drug-delivery system is described which can serve as a platform for the topical delivery of a wide variety of therapeutic agents to the skin. Specifically, a topical external analgesic gel contains ketoprofen, a skin penetration enhancer/cosolvent, a thickening agent and a base to adjust pH. The formulation uses a relatively small number of safe components and is easy to prepare with a high yield of finished product. The chemical stability of ketoprofen in the gel and the physical stability of the gel itself ensure a satisfactory shelf-life for the product. The gel is aesthetically pleasing (i.e., easy water-washability, non-irritating to skin, non-staining of clothing, etc.) and has proven to provide rapid relief of musculoskeletal pain, thereby helping to ensure patient compliance.

18 Claims, No Drawings

(56) References Cited

OTHER PUBLICATIONS

Barkin, R.L., Topical nonsteroidal anti-inflammatory drugs: The importance of drug, delivery, and therapeutic outcome, Amer. J. Ther. Feb. 22, 2012.
Beetge, E., du Plessis, J, Müller, D.G., Goosen, C., van Rensburg, F.J., The influence of the physicochemical characteristics and pharmacokinetic properties of selected NSAID's on their transdermal absorption. Int. J. Pharmaceut. 193: 261-264 (2000).
Bjorkman, D.J., Nonsteroidal Anti-inflammatory Drug-Induced Gastrointestinal Injury. Amer. J. Med. 101(Suppl. 1A): 25S-32S (1996).
Bonina, F.P. and Montenegro, L. Effects of some non-toxic penetration enhancers on in vitro heparin skin permeation from gel vehicles. Int. J. Pharmaceut. 111: 191-196 (1994).
Bystrianyk, R., More hospitalized from NSAID bleeding than all American war casualties, Health Sentinel, 16:00 (Jan. 10, 2010).
Ceschel, et al., Correlation Between the Transdermal Permeation of Ketoprofen and its Solubility in Mixtures of a pH 6.5 Phosphate Buffer and Various Solvents, Drug Delivery, 2002, vol. 9, No. 1, pp. 39-45 (summary only).
Coaccioli, S., Ketoprofen 2.5% gel: a clinical overview, Eur. Rev. Med. Pharmacol. Sci. 15: 943-949 (2011).
Cordero, J.A., Alarcon, L., Escribano, E., Obach, R., Domenech, J., A comparative study of the transdermal penetration of a series of nonsteroidal anti-inflammatory drugs, J. Pharm. Sci. 86: 503-507 (1997).
Cordero, J.A., Camacho, M., Obach, R., Domenech, J., Vila, L., In vitro index of topical anti-inflammatory activity to compare a series of NSAIDs. Eur. J. Pharm. Biopharm. 51: 135-142 (2001).
Desai, D.D., Hasman, D.F., Schmucker-Castner, J.F., Advances in Carbomer polymer technology, BF Goodrich, Specialty Chemicals, Cleveland, OH 44141.
Dreiser, R.L., Topical antirheumatic drug therapy: current practice and future trends. Eur. J. Rheumatol. Inflamm. 14: 3-8 (1994).
European Medicines Agency (EMEA) Press Release http://www.emea.eu.int.
Fabin, B., and Touitou, E., Localization of lipophilic molecules penetrating rat skin in vivo by quantitative autoradiography. Int. J. Pharm. 74: 59-65 (1991).
FDA Issues Public Health Advisory Recommending Limited Use of Cox-2 Inhibitors, FDA Talk Paper, Dec. 23, 2004.
Flouvat, B., Roux, A., Delhotel-Landes, B., Pharmacokinetics of ketoprofen in man after repeated percutaneous administration, Arzneim. Forsch. 39: 812-815 (1989).
Gavura, S., Anti-inflammatory drugs: A closer look at the risks, Science-Based Medicine, Mar. 15, 2013.
Grahame, R. Transdermal non-steroidal anti-inflammatory agents, Brit. J. Clin. Pract. 49: 33-35 (1995).
Gürol, Z., Hekimoğlu, S., Demirdamar, R., Şumnu, M. Percutaneous absorption of ketoprofen. I. In vitro release and percutaneous absorption of ketoprofen from different ointment bases. Pharm. Acta Helv. 71: 205-212 (1996).
Hadgraft, J., du Plessis, J., Goosen, C., The selection of non-steroidal anti-inflammatory agents for dermal delivery. Int. J. Pharmaceut. 207: 31-37 (2000).
Harris, R.H. and Vavra, I., "Ketoprofen", Anti-Inflammatory and Anti-Rheumatic Drugs, vol. II. (Ed., Rainsford, K.D.), CRC Press, Inc., Boca Raton, FL (1985).
Harrison, J.E., Watkinson, A.C., Green, D.M., Hadgraft, J., Brain, K., The relative effect of Azone® and Transcutol® on permeant diffusivity and solubility in human stratum corneum. Pharm. Res. 13: 542-546 (1996).
Knox, R., World's most popular painkiller raises heart attack risk, NPR, Feb. 12, 2013. http://www.npr.org/blogs/health/2013/02/12/171832741/.
Lawrence, R.C., Felson, D.T., Helmick, C.G., Arnold, L.M., Choi, H., Deyo, R.A., Gabriel, S., Hirsch, R., Hochberg, M.C., Hunder, G.G., Jordan, J.M., Katz, J.N., Kremers, H.M. and Wolfe, F., Estimates of the prevalence of arthritis and other rheumatic conditions in the United States. Part II. Arthritis Rheum.58(1):26-35 (2008). doi: 10.1002/art.23176.
Mason, L., Moore, R.A., Derry, S. and McQuay, H.J., Topical NSAIDs for acute pain: a meta-analysis, BMC Family Practice 5:10 (2004). doi:10.1186/1471-2296-5-10; This article can be found online at:http://www.biomedcentral.com/1471-2296/5/10.
Massey, T., Derry, S., Moore, R.A. and McQuay, H.J., Topical NSAIDs for acute pain in adults, Cochrane Database Syst. Rev. Jun. 16, 2010;(6):CD007402. doi: 10.1002/14651858.CD007402.pub2.
McGettigan P, Henry D., Use of non-steroidal anti-inflammatory drugs that elevate cardiovascular risk: an examination of sales and essential medicines lists in low-, middle-, and high-income countries, PLOS Med.10 (2):Feb. 12, 2013. e1001388.doi:10.1374/journal.pmed.1001388.
McNeill, S.C., Potts, R.O., Francoeur, M.L. Locally enhanced topical delivery (LETD) of drugs: does it truly exist? Pharm. Res. 9: 1422-1427 (1992).
Meek, I.L., van de Laar, M.A.F.J. and Vonkeman, H.E., Non-steroidal anti-inflammatory drugs: An overview of cardiovascular risks, Pharmaceuticals, 3: 2146-2162 (2010).
Meloun M, Bordovská S, Galla L. The thermodynamic dissociation constants of four non-steroidal anti-inflammatory drugs by the least-squares nonlinear regression of multiwavelength spectrophotometric pH-titration data. J. Pharm. Biomed. Anal. 45: 552-564 (2007).
Merck Announces Voluntary Worldwide Withdrawal of VIOXX®, Merck and Co., Inc., Whitehouse Station, NJ, Sep. 30, 2004.
Moore, R.A., Tramer, M.R., Carroll, D., Wiffen, P.J., McQuay, H.J. Quantitative systematic review of topically applied non-steroidal anti-inflammatory drugs, BMJ 316: 333-338 (1998).
Panchagnula, R. and Ritschel, W.A., Development and evaluation of intracutaneous depot formulation of corticosteroids using Transcutol as a cosolvent: in vitro, ex-vivo and in vivo rat studies. J. Pharm. Pharmacol. 43: 609-614 (1991).
Panchagnula, R., Development of an intracutaneous depot for drugs, Ph.D. Dissertation, University of Cincinnati (1991).
Patel, R.K., Leswell, P.F., Comparison of ketoprofen, piroxicam, and diclofenac gels in the treatment of acute soft-tissue injury in general practice. Clin. Ther. 18: 497-507 (1996).
Péhourcq, F., Matoga, M., Jarry, C., Bannwarth, B., Study of the lipophilicity of arylpropionic non-steroidal anti-inflammatory drugs. A comparison between LC retention data on a polymer-based column and octanol-water partition coefficients, J. Liq. Chrom. & Rel. Technol. 24: 2177-2186 (2001).
Reddy, K.S., Roy, A., Cardiovascular Risk of NSAIDs: Time to Translate Knowledge into Practice. PLOS Med 10(2): Feb. 12, 2013. e1001389. doi:10.1371/journal.pmed.1001389.
Ritschel, W.A. and Hussain, A.S., In vitro skin penetration of griseofulvin in rat and human skin from an ointment dosage form. Arzneim. Forsch. /Drug Res. 38: 1630- 1632 (1988).
Ritschel, W.A. and Hussain, A.S., Influence of selected solvents on penetration of griseofulvin in rat skin, in vitro. Pharm. Ind. 50: 483-486 (1988).
Ritschel, W.A., Panchagnula, R., Stemmer, K., Ashraf, M., Development of an intracutaneous depot for drugs. Skin Pharmacol. 4: 235-245 (1991).
Sarzi-Puttini P, Atzeni F, Lanata L, Bagnasco M., Efficacy of ketoprofen vs. ibuprofen and diclofenac: a systematic review of the literature and meta-analysis, Clin. Exp. Rheumatol., 31(5):731-738 (2013). Epub May 17, 2013.
Shah, V.P., Behl, C.R., Flynn, G.L., Higuchi, W.I., Schaefer, H., Principles and criteria in the development and optimization of topical therapeutic products. J Pharm Sci. 81: 1051-1054 (1992).
Shah, V.P., Behl, C.R., Flynn, G.L., Higuchi, W.I., Schaefer, H., Principles and criteria in the development and optimization of topical therapeutic products, Int. J. Pharmaceut. 82: 21-28 (1992).
Shah, V.P., Behl, C.R., Flynn, G.L., Higuchi, W.I., Schaefer, H., Principles and criteria in the development and optimization of topical therapeutic products, Pharm. Res. 9: 1107-1111 (1992).
Singh, P., Roberts, M.S., Skin permeability and local tissue concentrations of non-steroidal anti-inflammatory drugs after topical application, J. Pharmacol. Exp. Ther. 268: 144-151 (1994).

(56) References Cited

OTHER PUBLICATIONS

Smith, A., Pfizer pulls Bextra off the market, CNN Money, Apr. 7, 2005. http://money.cnn.com/2005/04/07/news/fortune500/bextra/.

Touitou, E., Levi-Schaffer, F., Shaco-Ezra, N., Ben-Yossef, R., Fabin, B., Enhanced permeation of theophylline through the skin and its effect on fibroblast proliferation. Int. J. Pharm. 70: 159-166 (1991).

Vaile, J.H., Davis, P. Topical NSAIDs for musculoskeletal conditions, a review of the literature, Drugs 56: 783-799(1998).

Wiegand, T.J. and Tarabar, A., Nonsteroidal anti-inflammatory agent toxicity, Medscape, Nov. 14, 2012.http://emedicine.medscape.com/article/816117.

W. Xiaomin, W. Longping, Transdermal delivery of nonsteroidal anti-inflammatory drugs mediated by polyamidoamine (PAMAM) dendrimers, J. Pharm. Sci., 96: 595-602 (2007).

Yazdanian, M. and Chen, E., The effect of diethylene glycol monoethyl ether as a vehicle for topical delivery of ivermectin. Vet. Res. Commun. 19: 309-319 (1995).

* cited by examiner

GEL FOR TOPICAL DELIVERY OF NSAIDS TO PROVIDE RELIEF OF MUSCULOSKELETAL PAIN AND METHODS FOR ITS PREPARATION

FIELD OF THE INVENTION

This invention comprises pharmaceutical compositions useful for the topical administration of a wide variety of poorly water-soluble drugs used to treat a variety of therapeutic indications where topical therapy is the preferred method of drug administration. The invention will be described in particular in connection with analgesic gel compositions containing non-steroidal anti-inflammatory drugs (NSAIDs) that are to be applied by a patient to the skin overlying affected areas to provide relief of inflammation and pain in rheumatoid arthritis, osteoarthritis, soft tissue injuries, strain, sprain and sports injuries, although other uses are contemplated.

BACKGROUND OF THE INVENTION

NSAIDs are the most widely used medications in the world. Their use can start as early as infancy for treating pain and fever and can continue into senescence where they are standard therapy for treating osteoarthritis and other musculoskeletal conditions (1). The mechanism for both the therapeutic anti-inflammatory, analgesic and antipyretic actions as well as the undesired side-effects of non-steroidal anti-inflammatory drugs (NSAIDs) on the stomach and kidneys is primarily mediated through their inhibition of cyclooxygenase (COX), the rate-limiting enzyme in the synthesis of prostaglandins. COX exists in two isoforms, known as COX-1 and COX-2, which have different structures and functions. COX-1 is involved in a number of reactions, including the production of prostacyclin, which is both antithrombogenic and, in the gastric mucosa, cytoprotective. COX-2 is believed to be induced by inflammatory mediators and has a pathophysiological role in inflammation. The beneficial anti-inflammatory effects of the NSAIDs are believed to be mediated by the inhibition of COX-2, while the inhibition of COX-1 produces the undesirable gastrointestinal side effects. A more detailed review of these mechanisms and their impact on the use of NSAIDs is provided by Meek et al. (2).

The first generation NSAIDs which were successfully marketed as both prescription and over-the-counter (OTC) medications are relatively non-specific for COX-2 and also produce significant inhibition of COX-1, thereby decreasing its protective effect on the gastrointestinal mucosa. NSAID therapy reportedly is associated with upper gastrointestinal (GI) symptoms in 25% of patients, causes ulcers or erosions in 40% of patients, increases the risk of ulcer bleeding or perforation three- to fourfold, and increases the rate of hospitalization or death from GI complications fivefold. NSAID therapy is also associated with lower GI complications, i.e., 10-15% of NSAID users experience diarrhea. Furthermore, the risk of intestinal ulceration, erosion, perforation, and stricture formation increases in patients taking NSAIDs. Treatment and prevention of these adverse GI effects dramatically increase the cost of NSAID therapy (2). It has been estimated (3) that oral NSAIDs are responsible for over 100,000 hospitalizations due to gastrointestinal bleeding and more than 16,000 deaths per year, resulting in hospitalization costs of $2 billion annually.

As a result of these shortcomings a large body of research has been directed towards finding NSAIDs which would be specific for COX-2. The result of these efforts was the introduction in the late 1990's of a number of compounds with more specific COX-2 inhibition such as rofecoxib (Vioxx®), celecoxib (Celebrex®), and valdecoxib (Bextra®). Unfortunately, the long-term use of these agents has demonstrated serious cardiovascular consequences such as myocardial infarction and stroke. These adverse events prompted Merck to recall Vioxx® from the US market on Sep. 30, 2004 (4). Shortly thereafter, on Apr. 7, 2005, Bextra® was also withdrawn from the US and European Union (EU) markets (5). These events were significant as Celebrex® with $3.3 billion in sales in 2004, and Bextra® with $1.3 billion in 2004 sales, were among Pfizer's top selling products (5). The FDA also requested that manufacturers of all NSAIDs make labeling changes to their products so that the package inserts include a "boxed warning" highlighting the potential for increased risk of cardiovascular events and the well described, serious, potentially life-threatening gastrointestinal bleeding associated with their use. The Celebrex® labeling was to contain, in addition to the general labeling that would apply to all NSAIDs, safety data from long-term treatment trials with celecoxib. A meta-analysis of data regarding NSAID use in 15 countries representing high-, medium-, and low-incomes was recently performed (6). This study suggests that, among traditional NSAIDS, oral diclofenac may carry the highest risk of adverse cardiovascular (CV) events and death (6). The study concluded that oral diclofenac use carried a CV risk equivalent to Vioxx®, in at-risk populations. The researchers suggested that diclofenac should be removed from national essential medicines lists (EMLs) and that it's marketing authorization should be revoked globally. Others (7,8) who commented on this article exhibited both dismay and great concern as to why diclofenac continues to be the most widely recommended NSAID in the world (found on the EML of 74 countries) while a potentially safer alternative such as naproxen is found on the EML of only 27 countries.

These examples illustrate that there is a substantial need for alternate delivery systems for NSAIDs that can minimize these life-threatening adverse events.

DESCRIPTION OF THE PRIOR ART

Pain relief for sore and/or stiff joints and muscles has been addressed in the past with topically applied preparations. Specifically, it is known that aches and pains related to sore and/or stiff joints and muscles can be relieved by applying topical creams and lotions.

Most of the known topical NSAID preparations have utilized lower alcohols (i.e., ethanol, isopropanol, or combinations thereof) as cosolvents. It is recognized that these volatile agents can evaporate before or after application of the preparation. This can result in the partial precipitation of the active ingredient from the preparation onto the skin surface which will result in an unsightly residue on the skin from which little or no absorption of the drug into the skin is possible.

Although these preparations provide varying levels of pain relief, their use can lead to a variety of problems. First, the lower alcohols are known to have a high potential to cause drying and delipidisation of the skin resulting in skin irritation, especially on sensitive regions of the body. This factor limits the amount of these preparations which can be applied to the skin and the length of time for which they can be applied. Application to broken skin is especially problematic with these preparations.

Many of these preparations have an undesirable odor which is difficult to mask.

Many of the existing topical preparations have a runny consistency and a greasy feel and do not blend into the skin very rapidly or completely.

Moreover, many of these previous topical preparations can stain clothing and are very difficult to remove by washing with water.

All of the above factors can lead to an unacceptable level of patient compliance. It is clear from reading the literature on NSAID dosage form development that a significant number of researchers have confused the principles of "topical" and "transdermal" delivery in both published research articles and patents. On numerous occasions one can find references to the development of transdermal delivery systems of NSAIDs which are purported to "minimize the systemic toxicities associated with oral NSAID therapy". These inaccurate statements persist today despite the fact that in a workshop held in March of 1990, sponsored jointly by the American Association of Pharmaceutical Scientists (AAPS) and the U.S. Food and Drug Administration (FDA), a committee of experts in this field clearly delineated the distinction between these two terms (9). These authors emphasized the critical importance of making a clear distinction between these terms and repeated their concerns on at least two subsequent occasions (10, 11). A topical medication is intended to have an effect locally at or beneath the site of application where the goal is to get the drug into the skin where it can be retained. Topical medications are designed to avoid significant drug concentrations in the blood, and to cause fewer adverse reactions and fewer drug interactions with other medications the patient may be taking concurrently. Examples of topical medications include antibiotics for skin infections, corticosteroids for skin irritation, and some anesthetics. Transdermal medications are designed to deliver drugs through the skin and into the bloodstream to achieve systemic effects and to have an effect in areas of the body distant from the site of application. Transdermal administration is an excellent method to use when a patient is unable to swallow or for medications that are significantly metabolized by first-pass metabolism in the gut or the liver. Transdermal delivery is frequently utilized for anti-nausea drugs, hormone replacement therapy, and generalized pain. The following are some examples of patents and publications using the term "transdermal" incorrectly. Many more examples of this confusion can be found throughout the literature.

H. W. Jun and L. Kang, Composition and method for enhanced transdermal absorption of nonsteroidal anti-inflammatory drugs, U.S. Pat. No. 6,368,618 B1.

K. Shah, Composition for transdermal administration of non-steroidal anti-inflammatory drug, EP 2,654,638 A1.

R. J. Gabach, A. F. Scasso, F. J. E. Stefano, Transdermal device comprising non-steroidal anti-inflammatory drugs incorporated in acrylic adhesive polymer matrix, EP 1,158,967 B1.

W. Xiaomin, W. Longping, Transdermal delivery of non-steroidal anti-inflammatory drugs mediated by polyamidoamine (PAMAM) dendrimers, J. Pharm. Sci., 96: 595-602 (2007).

G. C. Ceschel, P. Maffei, and S. Lombardi Borgia, Correlation Between the Transdermal Permeation of Ketoprofen and its Solubility in Mixtures of a pH 6.5 Phosphate Buffer and Various Solvents, Drug Delivery, 9: 39-45 (2002).

U.S. Pat. No. 5,093,133 by Wisniewski and Gemborys (1990) describes a method for topical delivery of ibuprofen to treat inflammation and/or pain in the joints or soft tissue below the skin. The described percutaneous delivery system consists of ibuprofen incorporated into a hydroalcoholic gel having a pH of 3.5 to 6.0. Ibuprofen is not a preferred NSAID for topical delivery as a number of authors have previously reported. Moreover, ibuprofen has a pKa of 4.4 and thus its fraction unionized could range from 88.8% at pH 3.5 (good) to 2.45% at pH 6.0 (not good). Based upon our own experience with ketoprofen (pKa 4.30) a pH of 5 or less would provide >20% of ibuprofen in the unionized form which is the preferred form due to its enhanced ability to penetrate the stratum corneum. U.S. Pat. No. 6,723,345 B2 by Drizen et al. (2004) describes a sterilized gelled polymer matrix composed of a highly negatively charged polymer such as sodium hyaluronate and a nonionic polymer such as hydroxyethyl cellulose along with benzyl alcohol, methoxypolyethylene glycol (MPEG) into which a salt form of diclofenac is incorporated. This "transdermal" delivery system is purported to provide a major alternative to oral NSAID therapy, especially for those individuals who have a history of undesirable side-effects associated with gastric and intestinal irritation. Also for those patients who have already suffered damage, including ulceration and loss of absorption from the intestinal tract, the transdermal preparations described present a new way of providing effective treatment and relief of painful symptoms. The authors note that an occasional patient will experience mild stomach upset from the transdermal preparation which they describe, but the effect would be transient and of mild severity. Once again this statement illustrates their confusion regarding the definition of "transdermal". Their "transdermal" delivery system is designed to deliver therapeutic levels of a drug to specific sites below the dermal level of the skin including, but not limited to, knees, ankles, hands, feet and neck. Transdermal delivery of diclofenac was substantiated by: 1. Measurable blood levels of diclofenac, 2. Diclofenac presence in the urine of patients treated with the transdermal, 3. The presence of diclofenac in synovial fluid where joints with synovial fluid are target sites for treatment. 4. Rapid absorption following topical administration, and 5. Rapid relief of painful symptoms in a significant number of patients already being treated with the products. The authors describe how the drug must be suspended or entrapped in a specially designed polymer matrix containing a specific molar ratio of negatively charged polymers and non-ionic polymer suspended or dissolved in water and solubilizers. Although the formula is not overly complex the authors provide no explanation as to why the formula must be prepared in sterilized glass vessels and there is no discussion of its aesthetic features or how well it is accepted by patients.

U.S. Pat. No. 6,083,996 by Buyuktimkin et al. (2000) describes topical compositions for NSAID delivery in which an aqueous pharmaceutical composition of a semi-solid consistency is provided for topical application. The composition comprises one or more NSAIDs, a non-basic polymeric skin penetration enhancer and a lipophilic solvent. The polymeric skin penetration enhancer is present in an amount sufficient to enhance skin penetration of the NSAID. The lipophilic solvent is a mixture of an aliphatic $C_2$ to $C_8$ alcohol and an aliphatic $C_8$ to $C_{30}$ ester. The composition may also include a thickening agent, an emulsifying agent and/or a buffer system capable of providing a buffered pH value in the range of about 3 to physiological. In a preferred composition, the NSAID is an ibufenac group drug (e.g., ibuprofen) and the polymeric skin penetration enhancer is a galactomannan gum. It should be noted that these authors state that the preferred pH range is from about pH 4.5 to about 5.5 when the NSAID is ketoprofen. These values are consistent with the preferred pH of 4.5 to 5.3 noted in our invention.

US Application 2009/0053290 A1 by Sand et al. (2009) describes an invention that is directed to the "transdermal" delivery of a variety of drugs and compositions. In one embodiment of the invention, in fact, a transdermal delivery composition is provided that includes at least two penetrants working synergistically but by disparate biochemical pathways. In an exemplary embodiment, the transdermal delivery composition includes both benzyl alcohol and lecithin organogel. The authors note that these two penetrants provide an effective means of transdermally delivering a wide variety of payloads through the epidermis and stratum corneum. In addition, they note how this effective means of "transdermal" transport of drugs, agents and compositions makes the delivered agent more "bioavailable" in smaller doses and increases bio activity. This, in turn, reduces the side effects normally associated with the target drug or agent and reduces systemic toxicity. Once again, these authors confuse the meaning of the term "transdermal". In fact, "effective transdermal transport" would likely increase side effects and increase systemic toxicity. Throughout this application a number of naïve statements are made, the most striking of which is in claim 62 where they claim to use an NSAID at a concentration "from 0.1% to about 80% by weight". Clearly, there is no way to incorporate this high a concentration into a dosage form. More importantly there is no need to use an NSAID concentration anywhere near 80% w/w. Any concentration exceeding about 10-15% w/w is strictly wasteful. Other perplexing statements (section 0054) include the comments that "Lecithin organogels are suitable for cosmetic and pharmacologic applications" and "lecithin organogels can be prepared easily and rapidly". The preparation of PLO gel is a time-consuming process which results in a product that is aesthetically unpleasing. Finally, the suggestion to use "carbitol solvent (available from Union Carbide)" as a "suitable penetrant" is incorrect as carbitol (as supplied by Union Carbide) is insufficiently pure to be approved for human use by any regulatory body.

Grasela et al. (1998) in U.S. Pat. No. 5,837,289 described a formulation for topical delivery consisting of two penetration enhancers which function synergistically to provide for a rapid but controllable transport of the medication from the cream into the skin. These authors propose a formulation which employs a Pluronic Lecithin Organogel (PLO) gel. Others (e.g., G. Cevc and U. Vierl (2009) in U.S. Pat. No. 7,473,432 B2) stated that this type of formulation is generally a poor membrane destabilizer and serves merely as a superficial reservoir for drug applied to skin. Our own experience in formulating PLO gels is that they are time-consuming to prepare (e.g., the Pluronic component must be stored for several hours in a refrigerator to ensure complete dissolution), the Pluronic component can support mold growth and requires the inclusion of a preservative, and the sensory properties are aesthetically unpleasing. These factors make other choices of a drug-delivery vehicle more appealing.

U.S. Pat. No. 4,188,373 by Krezanoski (1980) describes an invention in which Pluronic polyols are used in aqueous compositions to provide thermally gelling aqueous systems. Adjusting the concentration of the polymer provides the desired sol-gel transition temperature, i.e., the lower the concentration of polymer, the higher the sol-gel transition temperature. It should be noted that there is a critical concentration minimum below which a gel will not form. The use of an aqueous liquid which can be applied at room temperature as a liquid but which forms a semi-solid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. However, the oil phase which usually consists of lecithin and isopropyl palmitate is typically prepared by allowing this mixture to stand overnight to ensure complete dissolution. In addition, the aqueous phase consists of Pluronic F-127 dissolved in ice cold water, placed in a refrigerator, and mixed periodically over several hours to ensure complete dissolution. In addition, the Pluronics are subject to mold growth and must be preserved. The lengthy and complex nature of the manufacturing process makes this approach less attractive than other dosage form options.

Similar drug delivery systems which utilize thermosetting gels are described in U.S. Pat. No. 4,474,751 by Haslam et al. (1984) and U.S. Pat. No. 4,478,822 by Haslam et al (1984). The important feature of these systems is that both the gel transition temperature and/or the rigidity of the gel can be modified by adjusting the pH and/or the ionic strength, as well as by adjusting the concentration of the polymer. Other patents disclosing pharmaceutical compositions which rely upon an aqueous gel composition as a vehicle for the application of the drug include the following: U.S. Pat. No. 4,767,619 by Murray (1988) describes an aqueous coating gel which dries to form a continuous burn wound-adherent film in situ. U.S. Pat. No. 4,511,563 by Schmolka (1985) describes the preparation of a clear analgesic gel which is non-tacky comprising an analgesic, nonionic surfactants, glycerin and water. U.S. Pat. No. 4,861,760 by Mazuel and Friteyre (1989) describes an ophthalmological composition intended to be administered as a non-gelled liquid form which gels in situ. The gelling agent used is gellan gum. U.S. Pat. No. 5,318,780 by Viegas et al. (1984) also describes a composition for ophthalmic use which forms a gel in situ. The preparation comprises an ionic polysaccharide, a film-forming polymer, a medicament, and water. In contrast, U.S. Pat. No. 4,883,660 by Blackman and Ralske (1989) describe a non-aqueous gel base for topical, transmucosal and oral delivery.

King-Smith et al. (2013) in U.S. Pat. No. 8,470,886 describe a topical formulation comprising ibuprofen in a hydroalcoholic-based solvent system containing triethyl acetate and a surfactant. They further describe a physical stability of the formulation over "more than 1 month" at ambient temperature, a figure which is both vague and unimpressive in terms of providing a suitable shelf-life estimate. They also claim a colorless and odorless product which has a pH of "about 6.5". The authors further claim to use 20-50% w/w of alcohol which subjects their formulation to the criticisms of skin delipidisation and/or irritation and the possibility of significant evaporation when applied to the skin or in the container. In addition, a pH of 6.5 would result in only a very small fraction (0.79%) of the ibuprofen (pKa 4.4) being in its preferred unionized form which should penetrate the non-polar stratum corneum barrier more readily. Finally, a number of studies have pointed out that ibuprofen is not a preferred NSAID for topical delivery.

None of the above references disclose a gel containing ketoprofen in a formulation consisting of one of the newer carbomer derivatives (i.e., Ultrez 10, 20, 21 or 30), all of which have advantages over previously used Carbopol® derivatives including, their ease of dispersing, their outstanding sensory characteristics, and their unique rheological features which greatly facilitate and simplify the industrial manufacturing process. In addition, many of the earlier Carbopols, e.g., Carbopol 934, 934P, 940 and 941 utilized benzene (a known carcinogen) during the manufacturing process. The carbomers utilized in this invention, i.e., Ultrez 10, 20, 21 and 30, were developed to provide a safer polymerization solvent system and an easy-to-disperse product. Furthermore, none of these references disclose a formulation which utilizes Transcutol P in a dual role as a cosolvent and a penetration enhancer capable of providing LETD through the formation of intracutaneous depots in the skin. None of the above cited patents teach or suggest the use of the method or composition outlined in the present invention. In fact, although all of the patents studied list the components comprising their invention, a significant number of them fail to describe any details regarding a preferred method of preparation for their invention.

In addition, much of the prior art suffers from one or more shortcomings, including:

(a) A fundamental misunderstanding of the definition of the terms "topical" and "transdermal".

(b) A lack of any discussion concerning the chemical stability of the drug they are using in the delivery system which they propose.

(c) A lack of any discussion regarding the physical stability (e.g., syneresis, creaming, cracking, evaporation, etc.) of their proposed dosage form.

(d) A lack of discussion regarding the aesthetic appeal of the dosage form proposed which is a critical factor in helping to ensure patient compliance.

(e) An apparent lack of concern for the complexity of the manufacture of the dosage form. For example, technically-demanding preparations, large numbers of components, and percentage yields of the manufacturing process for the dosage form are rarely discussed.

(f) An apparent lack of concern for the patient-acceptability of the dosage form and hence patient compliance in their discussions. Factors affecting patient compliance with a dosage form include not only its ability to produce a satisfactory therapeutic outcome but also its aesthetic appeal (e.g., does the preparation look and feel pleasant? can it be washed off the skin easily? does it stain clothing?) and its cost.

(g) A great deal of the prior art involves formulations which utilize ethanol and/or isopropanol to dissolve the drug without any apparent concern for the fact that these volatile solvents can evaporate when applied to the patient's skin or in the container during storage. Such evaporation can result in a precipitate which not only looks unsightly on the skin but can also destabilize the formulation and may render it ineffective.

(h) Finally, some authors report a pH value for their formulations which would cause the NSAID to be in a predominantly ionized form with only a very small fraction being in the preferred nonionized form which has an enhanced ability to penetrate the non-polar stratum corneum barrier. This reduced ability to penetrate the stratum corneum could lead to a slower onset of action and possibly an insufficient amount of the applied drug reaching its site of action resulting in a limited therapeutic effect.

Rationale for a Topical Nsaid Delivery System

As used here the term "topical" refers to a semisolid preparation (e.g., ointment, cream, or gel) to be applied onto the surface of the skin to provide an effect (e.g., pain relief) locally at or beneath the application site.

Although topical NSAID preparations had been used for decades in Europe, the United Kingdom, and elsewhere the recalls of Vioxx® and Bextra® resulted in a renewed interest in them in North America. As a result of this increased interest a patch containing diclofenac (Flector®) was approved by the FDA on Jan. 31, 2007 followed by the FDA approval on Oct. 17, 2007 of a topical gel containing diclofenac sodium (Voltaren Emulgel®) Finally, a solution for topical use containing diclofenac sodium (Pennsaid®) was approved by the FDA on Nov. 4, 2009.

It is generally accepted that topical NSAID administration is a safer means of NSAID delivery than the oral route (12, 13). When a topical NSAID formulation is applied to the skin, its effectiveness depends upon the absorption of the drug across the stratum corneum and its penetration in sufficient quantities into the underlying inflamed tissues such as muscle, tendon sheath, and the synovium and synovial fluid of superficial articular compartments. The fundamental concept underlying the use of a topical delivery system for NSAIDs is that the drug will be rapidly transported via percutaneous absorption beneath the site of application and produce a significantly higher local tissue concentration than will be obtained with oral administration. In addition, the systemic drug concentrations attained following the topical application of an NSAID will be significantly lower (typically about 5% or less) than those observed following an oral therapeutic dose of the drug. The difference in systemic NSAID levels following topical dosing will result in a reduction in adverse events compared to those seen with oral dosing. This concept has been referred to as locally enhanced topical delivery, LETD (14). LETD has further been documented for a number of topically applied NSAIDs by several research groups (15-19).

Topical formulations can achieve LETD in a variety of ways, including the use of occlusion, the addition of penetration-enhancing agents, and the use of different molecular entities than those used in equivalent oral formulations (20). One mechanism whereby LETD has been reported to occur is via the formation of intracutaneous depots in the skin. Conceivably, these depots may allow a drug to largely bypass the blood capillaries present at the epidermal-dermal junction in the skin. This phenomenon would thereby permit therapy of deep tissues beneath the site of drug administration. Such depot formation has been reported for corticosteroids (21), griseofulvin (22), and ivermectin (23) in topical formulations containing the cosolvent Transcutol. Topical drug delivery can also provide other benefits, including less frequent dosing, better control of drug release, and an increased ability to target delivery of the NSAID to specific tissue sites. An additional benefit of the lower blood levels of NSAID following topical delivery compared to those observed following oral dosing is the relatively low potential for drug interactions with other therapeutic agents in use by the patient. Furthermore, significant metabolism of the NSAID in the gut or the liver (i.e., the "first-pass" effect) is avoided, since the drugs do not pass through the gut or liver prior to reaching their site of action.

In a recent review (24) comparing topical therapies for treating osteoarthritis (OA) the authors noted that the European League Against Rheumatism (EULAR) and the National Institute for Health and Clinical Excellence (NICE) recommended the use of topical NSAIDs before oral therapies. The authors also noted that topical salicylates and capsaicin, available in the US without prescription, have not shown substantial efficacy in clinical trials and both have the potential to cause serious adverse events.

Wiegand and Tarabar (25) reported that more than 70 million prescriptions for NSAIDs are written each year in the United States. With over-the-counter (OTC) use included, more than 30 billion doses of NSAIDs are consumed annually in the United States. In 2005, OA was reported to affect 13.9% of adults aged 25 and older and 33.6% (12.4 million) of those over age 65 (26). This represents a total of 26.9 million adults in the US, up from 21 million in 1990. Since OA increases with age these figures seem destined to increase as the population ages.

The US pain management market is the largest single market in the world with sales of $13 billion. This comprises over half of the global pain market of $22 billion. In 2012, the US market for topical NSAIDs was estimated to be worth $500 million (27). These figures indicate that there is a significant opportunity for other topical NSAID products to gain a substantial market share in this field since a product with greater efficacy and lower cost than the current products would be attractive to patients, health professionals, and insurance providers.

Rationale for use of the Ingredients Chosen

1. Ketoprofen

All of the current topical NSAID products approved for use in the United States use diclofenac and all are quite expensive. A further issue with Voltaren Emulgel® is that the product is greasy, has a strong smell, and utilizes an emulsion formulation which is susceptible to physical instability (i.e., creaming or cracking), especially when subjected to abrupt changes in temperature. In addition, the recommended maximum dosage of 32 grams/day, results in an average cost to the patient of $196 per month (28).

As noted earlier, topical ketoprofen preparations have been used in Europe, the United Kingdom, Mexico and other countries for several years. Several studies (29, 30) have consistently demonstrated that ketoprofen is one of the best NSAIDs for topical administration. Hadgraft et al. (18) and others (19) have demonstrated that ketoprofen has the most rapid penetration into the skin and that rapid relief of pain can be achieved at a relatively low dose.

Ketoprofen is 2-(3-benzoylphenyl)-propionic acid. Its empirical formula is $C_{16}H_{14}O_3$, with a molecular weight of 254.29. Ketoprofen is a weak acid with a pKa of 4.30 (31) and a Log P (octanol: water) of 2.68 (32). Ketoprofen is a white or off-white, odorless, nonhygroscopic, fine to granular powder, melting at about 94° C. It is freely soluble in ethanol, chloroform, acetone, and ether and soluble in benzene and strong alkali, but practically insoluble in water at 20° C.

The efficacy of ketoprofen in the clinical treatment of inflammations and pain relief in rheumatoid arthritis, osteoarthritis, soft tissue injuries (33), and strain, sprain and sports injuries (20) has been reported. Because of its ability to inhibit both the cyclooxygenase and lipoxygenase pathways of arachidonic acid formation, ketoprofen has high analgesic potency and a rapid onset of action, i.e., 15 times higher potency than ibuprofen and 8-20 times greater than indomethacin and naproxen in the release of prostaglandin (34). The pharmacokinetics of ketoprofen following topical administration was studied by Flouvat et al. (17). Ketoprofen gel demonstrated a low systemic diffusion and excellent tolerance in the local treatment of inflammation.

Several head-to-head studies comparing topical formulations showed ketoprofen to be more effective than diclofenac (35-38). For example, Patel and Leswell (35) found a greater improvement in treatment of an injury following ketoprofen gel vs. diclofenac gel (38% vs. 30%). Massey et al. (36) compared topical ketoprofen to topical diclofenac in seven clinical studies and observed that, on average, 73% of study participants experienced relief of acute pain with ketoprofen vs. 52% for diclofenac. Other investigators (37, 38) have concluded that ketoprofen was significantly better than all other topical NSAIDs in indirect comparison. A recent review (39) summarized the findings of several studies employing a 2.5% ketoprofen gel which has been available in Europe for many years. The review included data from both clinical trials and in "real-life" practice. The findings reported included pharmacokinetic studies showing that serum levels of ketoprofen following the application of the 2.5% gel are less than 1% of those reported after oral dosing. A second major finding was that 100-300 mg of the gel applied twice daily produced a clinical benefit in the majority of patients with a broad range of symptoms. The author concluded that the 2.5% gel applied topically "appears to offer a more favourable therapeutic profile than oral NSAIDs in the management of soft tissue injuries" and "provides a good symptom relief at low plasma concentration, a favourable risk/benefit ratio, and a low incidence of AEs (Adverse Effects)." One recent study (40) concluded that "the efficacy of orally administered ketoprofen in relieving moderate to severe pain and improving functional status and general condition was significantly better than that of ibuprofen and/or diclofenac." In total, these studies indicate that ketoprofen is a safer and more effective NSAID than diclofenac in treating these inflammatory conditions and that ketoprofen gel is clearly one of the most promising of the topical NSAID formulations.

Ketoprofen for oral use is currently available on the U.S. market only as the generic ketoprofen. Former brand-named products that have been discontinued in the United States include: Orudis® an immediate-release capsule and Oruvail® an extended-release capsule. Orudis and Oruvail were indicated for the management of the signs and symptoms of rheumatoid arthritis and osteoarthritis. Oruvail was not recommended for treatment of acute pain because of its extended-release characteristics. Orudis was indicated for the management of pain and for the treatment of primary dysmenorrhea. Ketoprofen was also formerly available for OTC use as Actron® and Orudis KT® (in the form of 12.5 mg coated tablets).

The recommended initial dosage regimen for ketoprofen in patients with rheumatoid arthritis and osteoarthritis is 75 mg three times or 50 mg four times a day for the immediate-release, or 200 mg once-daily for the extended-release dosage form.

2. Transcutol P®

Transcutol® is also known as carbitol, 2-(2-ethoxyethoxy) ethanol, ethoxydiglycol or diethylene glycol monoethyl ether (DGME). Pharmaceutical grade DGME is a transparent liquid (MW 134.2) with unique solubilizing properties. It has the ability not only to solubilize both hydrophilic and hydrophobic materials, but also has penetration-enhancing properties. Furthermore, it is freely miscible with polar and nonpolar solvents. It is available from Dow Chemical in two grades, cosmetic grade which is >99.0% pure, and HP grade which is 99.5% pure. It also is marketed in a highly purified form containing >99.80% of DGME under the trade name Transcutol P (Gattefossé s.a., Saint Priest, Cedex, France), which is preferred. It has been used as a cosolvent in topical and parenteral products (41). Products currently marketed in the USA that contain Transcutol include Viractin Gel® and Shepard's Cream Lotion®. Several scientific papers have verified that Transcutol can increase significantly the flux of various compounds into and through the skin. Touitou et al (42) were able to enhance the flux of theophylline to the dermis. Fabin and Touitou (43) found that Transcutol could improve the skin permeation of tetrahydrocannabinol and modify the location of the drug within the skin. Harrison et al (44) investigated the mechanism of the permeation enhancement of Transcutol and suggested that its effect is due to a change in the solubility of the permeant in the skin. Ritschel and Hussain (45) concluded that Transcutol would be the penetration enhancer of choice if one had to deliver griseofulvin to the skin while decreasing its systemic uptake. Panchagnula and Ritschel (21) reported that the permeation of dexamethasone and hydrocortisone through the skin was decreased, and penetration into the skin increased, in the presence of Transcutol. They concluded that intracutaneous depots of drugs were formed. Yazdanian and Chen (23) investigated the permeation of Ivermectin through bovine skin and concluded that cutaneous depots of Ivermectin were formed in the presence of Transcutol. Panchagnula (46) used autoradiography to demonstrate the existence of intracutaneous depots.

3. Carbopol®

Carbopol® polymer is a product brand name of Lubrizol Corporation. There are a number of Carbopol® polymer grades which differ in their performance features. These grades are distinguished by a number designation following the brand names (e.g., Carbopol® 971P NF polymer and Carbopol® 71G NF polymer). In contrast, the term "Carbomer" is one of the generic names that can be used to describe Carbopol® polymers. Carbomer can be defined as a high molecular weight polymer of acrylic acid crosslinked with allyl ethers of polyalcohols. Topical preparations using various Carbopol® polymers have been available commercially for many years and the long-term safety of these substances is well established. In addition, they have a very low potential for causing skin irritation or skin sensitivity. In a comparison of four different bases a Carbopol® gel was shown to provide the fastest release rate and the greatest percutaneous absorption of ketoprofen (47). While Carbopols® have been in use for over forty years, Ultrez 10 was introduced about fifteen years ago in an attempt to overcome some of the shortcomings of the previous members of this series (48). Thus it does not appear in publications and patents occurring prior to the late 1990's. Carbopol® Ultrez 10 polymer was developed as the culmination of research to identify a safer (benzene-free) polymerization solvent system and easy-to-disperse interpolymer carbomer technologies. It is considered a "universal" polymer, as it is capable of replacing two or more carbomer polymer grades currently used to formulate lotions, creams or gels. Because of its universal rheology control characteristics (i.e., use a single polymer instead of two or more carbomer grades) and, in some formulation scenarios, its higher efficiency compared to traditional carbomer polymers, substantial cost savings in the manufacture of personal care products may be realized (49).

Recently other easy-to-disperse interpolymer carbomer derivatives in this category, with varying physical properties and added cosmetic appeal, have been introduced such as Ultrez 20, 21, and 30. Those skilled in the art will realize that these derivatives can be substituted for Ultrez 10 in various applications (including this one) without sacrificing the overall quality of the final formulation.

4. Triethanolamine (TEA)

Triethanolamine is supplied in a 99% pure form by Sigma Aldrich Company, St. Louis, Mo. It is one of several bases that can be used to neutralize the Carbopol® polymers present in the invention. Carbopol® polymers as supplied are dry, tightly coiled acidic molecules. Once dispersed in water, the molecules begin to hydrate and partially uncoil. Unneutralized dispersions have a pH range of approximately 2.5-3.5 depending on the polymer concentration. The unneutralized dispersions have very low viscosities, especially Carbopol® ETD and Ultrez™ polymers. The most common way to achieve maximum thickening from Carbopol® polymers is by converting the acidic Carbopol® polymer to a salt. This is easily achieved by neutralizing the Carbopol® polymer with a common base such as sodium hydroxide (NaOH) or triethanolamine (TEA). The neutralization ionizes the polymer and generates negative charges along the backbone of the polymer. Repulsions of like charges then cause uncoiling of the molecule into an extended structure. This reaction is rapid and gives instantaneous thickening and emulsion formation/stabilization. Optimum neutralization is achieved at a pH of 6.5-7.0, but is not necessary as sufficiently high viscosities can be achieved over a pH range of 4.5-9.0. This partial neutralization permits the dispersion to achieve sufficient viscosity and yield value to gain homogeneity and the suspension of aggregate particles in a continuous phase. This creates a space-filled homogeneous dispersion that doesn't phase separate.

5. Disodium EDTA Dihydrate

This salt form of EDTA (ethylenediaminetetraacetic acid) is used to chelate (bind) any ions that may be present. Excessive amounts of ions present in the formulation can destabilize the Carbopol® polymer and result in a loss in viscosity sufficient to render the gel unusable. Since water constitutes the major component of our formulation it is important to use deionized water to minimize the impact of any ions on the stability of the formulation.

6. Paragon III

In order to ensure the long-term stability of the formulation (and to ensure a shelf-life of ≥2 years) it is advisable to include a preservative in the formulation to ensure that mold and/or bacterial growth is avoided. Paragon III (Solvay USA, Cranbury, N.J. 08152) is a broad spectrum antibacterial which also protects against mold growth and has been used successfully by us for many years in a variety of different iterations of our Master Formula.

7. Fragrance

Although the formulation has no significant undesirable odor a small amount of a suitable fragrance can be added to ensure that any small amount of odor is masked. The most frequently utilized fragrance for this purpose which has proven to enhance the aesthetic appeal of the formulation is African Rain (Wellington Fragrance Company, Livonia Mich. 48150).

Rationale for the Formulation Chosen

The design of the vehicle chosen for topical delivery of any pharmacological agent is a critical factor in determining the efficacy of the final product (50). In addition to providing a stable medium for the active ingredient that provides a suitable shelf life for the product, the vehicle should also possess a number of other attributes. For example, the vehicle should enable the drug to be released rapidly onto the surface of the skin and should provide a medium that promotes the rapid penetration of the drug through the skin into the subcutaneous tissues. Furthermore, the vehicle itself should possess good physical stability such that there is only minimal evaporation of any cosolvents since excessive evaporation could lead to precipitation of the drug as an insoluble and unsightly film on the surface of the skin. If such a precipitate should form, as happens with many gel formulations, only minimal absorption of the drug can occur. This has been demonstrated with marketed gel formulations of NSAIDs as well as with estradiol gels.

The vast majority of topical NSAID products currently available use either ethanol, isopropanol, or both to help incorporate the water-insoluble drug into an aqueous vehicle. These volatile cosolvents have been omitted from this invention in order to avoid the evaporation and resultant drug precipitation out of the formulation. The vehicle should also provide a pleasant sensory experience in order to help ensure patient compliance. Other desirable attributes of the vehicle include a pleasant feel and fragrance, a rapid blending into the skin following application, a non-staining of clothing, and ease of removal when washing with water.

The vehicle chosen for our invention possesses all of the attributes discussed above and is easy to prepare. Furthermore, it uses a small number of ingredients which all have a high margin of safety, an important consideration in helping to minimize development and manufacturing costs as well as accelerating regulatory approval. This novel topical delivery system incorporates a penetration enhancer to assist in transporting the ketoprofen across the stratum corneum of the epidermis which is the primary barrier to percutaneous drug penetration.

The penetration enhancer allows the delivery of ketoprofen in sufficient quantities into the underlying inflamed tissues such as muscle, tendon sheath, the synovium and synovial fluid. The topically applied ketoprofen therefore will achieve the local relief of pain and inflammation without incurring the burden of high systemic plasma concentrations of the drug and the associated adverse events that often accompany oral NSAID therapy. An added benefit of the low blood levels of ketoprofen following topical delivery is the relatively low potential for drug interactions with other therapeutic agents in use by the patient. The invention described herein has proven to be effective in relieving musculoskeletal pain and is well tolerated by patients.

SUMMARY OF THE INVENTION

Given the side effects of oral NSAIDs, and the severe morbidity and mortality associated with COX-2 specific NSAIDs, alternative treatments are very important, particularly in the elderly. Consequently we have developed some topical NSAID gel formulations which have proven to be effective in relieving musculoskeletal pain and which are well tolerated by patients. Our novel formulation consists of a gel matrix into which we have incorporated a topical penetration enhancer. While not wishing to be bound by theory, it is believed that our penetration enhancer promotes the formation of intracutaneous depots of the active ingredient and thereby achieves Local Enhanced Topical Delivery (LETD). Penetration enhancers that can promote depot formation are ideally suited for topical therapies since they increase the concentration of the drug locally, i.e., at the site of application, but prevent the drug from being absorbed into the systemic circulation. A number of topical NSAID products are licensed for use in several European countries, including Great Britain, Italy and Germany. Some examples of commercial topical products containing ketoprofen are:

(a) Oruvail® (Rhone-Poulenc Rorer),
(b) Powergel® (G.D. Searle),
(c) Fastum® Gel (Menarini), and
(d) Gabrilen® Gel (Kreussler).

These and other commercially available formulations suffer from one or more serious drawbacks, e.g., complicated and expensive preparation steps or ingredients, wasteful drug overloading requirements, insufficient drug penetration, and poor aesthetic features of the formulation. Thus, there is a demonstrated need for improved, cost-effective compositions for topical delivery of NSAIDs.

Our aqueous semi-solid compositions are ideally suited for topical application. They consist of a non-steroidal anti-inflammatory drug (NSAID), a non-volatile skin penetration enhancer, a polymeric thickening agent, and an aqueous solvent. The penetration enhancer is present in an amount sufficient to dissolve the drug and to enhance skin penetration of the NSAID.

In a preferred composition, the NSAID is ketoprofen, the skin penetration enhancer is a pharmaceutical grade diethylene glycol monethyl ether (DGME), such as "Transcutol P", as supplied by Gattefossé, and the gelling (thickening) agent is a carbomer polymer, preferably a Carbopol® Ultrez polymer supplied by Lubrizol. The composition may also include a preservative, a neutralizing agent to raise the pH of the dispersion, a chelating agent, a fragrance, a preservative and, (optionally) a coloring agent.

The inventions described and claimed herein have many attributes and embodiments including, but not limited to, those described, set forth, or referenced in this Summary. The inventions described and claimed herein are not limited to or by the features of embodiments identified in this Summary. The Summary is included solely for purposes of illustration and not restriction.

In one embodiment of the invention the NSAID comprises Ketoprofen, alone, or in combination with, one or more additional NSAIDs selected from the group consisting of, but not limited to, flurbiprofen, ibuprofen, naproxen, fenoprofen, pirprofen, carprofen, oxaprozin, tiaprofenic acid, acetylsalicylic acid; diclofenac; diflunisal; etodolac; flufenamic acid; indomethacin; ketorolac; meclofenamate; mefenamic acid; nabumetone; oxyphenbutazone; phenylbutazone; piroxicam; meloxicam; salsalate, sodium salicylate; sulindac; tenoxicam; tolmetin and celecoxib.

In another embodiment of the invention the neutralizing agent is selected from the group consisting of Tromethamine, aminomethyl propanol, tetrahydroxypropylethylenediamine, sodium hydroxide and potassium hydroxide.

In another embodiment of the invention, the composition is adjusted to a pH in the range 4.5 to 5.3.

In another embodiment of the invention the preservative is selected from the group consisting of, but not limited to, DMDM Hydantoin, German Plus, Germaben II, methyl-, ethyl-, propyl-, and butyl- paraben, Euxyl K400, Bronopol, sodium benzoate, chlorhexidine, benzalkonium chloride, 2-phenoxyethanol, cetrimide, potassium sorbate, Paragon, and Paragon III.

In one preferred embodiment of the invention the chelating agent comprises ethylenediaminetetraacetic acid.

In yet another embodiment of the invention the composition further comprises a smooth muscle relaxant, such as cyclobenzaprine or dantrolene.

In still yet another embodiment of the invention, the composition further comprises an agent which can increase the blood flow to the site of administration, such as capsaicin, mustard oil, menthol, methyl salicylate, verapamil, diltiazem, and alprostidil.

In still yet another embodiment of the invention, the composition also includes one or more additional active agents, selected from the group consisting of an antihistamine such as diphenhydramine hydrochloride or chlorpheniramine maleate; a corticosteroid, a local anesthetic agent, a topical analgesic and an antibiotic; the corticosteroid is selected from the group consisting of hydrocortisone, a hydrocortisone-21-monoester, (such as hydrocortisone-21-acetates, hydrocortisone-21-butyrate, hydrocortisone-21-propionate, hydrocortisone-21-valerate, etc., and a hydrocortisone-17,21-diester, (such as hydrocortisone-17,21-diacetate, hydrocortisone-17-acetate-21-butyrate, hydrocortisone-17,21-dibutyrate), dexamethasone, flumethasone, prednisolone, methylprednisolone, clobetasol propionate, betamethasone benzoate, betamethasone dipropionate, diflorasone diacetate, fluocinonide, mometasone furoate, and triamcinolone acetonide, and the local anesthetic agent is selected from the group consisting of benzocaine, lidocaine, prilocalne and dibucaine; and the topical analgesic is selected from the group consisting of glycol salicylate, methyl salicylate, 1-menthol, d,1-camphor and capsaicin.

In still yet another embodiment of the invention, the composition further including in addition to or in replacement to the ketoprofen, one or more additional agents selected from the group consisting of benzocaine, tetracaine, mepivacaine, prilocalne, bupivacaine, lidocaine; acetaminophen, naproxen, ibuprofen, flurbiprofen, diclofenac, and salicylamide; an amebicide, a broad or medium spectrum antibiotic, an antifungal medication, penicillin, cephalosporin, a steroid, ACTH, an anabolic steroid, an androgenic steroid, a corticosteroid, glucocorticoid, gonadotropin, a gonadotropin-releasing human growth hormone, progesterone, progestogen, and progestogen and estrogen alone or in combination.

DETAILED DESCRIPTION OF THE INVENTION

Some examples of compositions which we have prepared and tested for their aesthetic properties as well as their efficacy in treating musculoskeletal pain are provided in Table I. These examples are given in order to provide those with ordinary skill in the art with a complete disclosure and description of how to make and use the invention and are not intended to limit the scope of the invention.

TABLE I

Examples of Four Typical Formulations (A, B, C, D) using Carbopol Ultrez Polymers

| Ingredients | Ingredient Composition (% w/w) Formulations | | | |
|---|---|---|---|---|
| | A | B | C | D |
| Ketoprofen, USP | 2.5 | 2.5 | 2.5 | 2.5 |
| Transcutol P, EP | 6.7 | 5.0 | 5.0 | 5.5 |
| Ultrez 10 | 1.0 | — | — | — |
| Ultrez 20 | — | 1.1 | — | — |
| Ultrez 21 | — | — | 0.9 | — |
| Ultrez 30 | — | — | — | 1.0 |
| Triethanolamine (99%) | 0.36 | 0.34 | 0.28 | 0.36 |
| Disodium EDTA Dihydrate | 0.05 | 0.06 | 0.06 | 0.06 |
| Paragon III | 0.6 | 0.6 | 0.6 | 0.65 |
| Fragrance | 0.43 | 0.5 | 0.5 | 0.51 |
| Deionized water | 87.56 | 89.9 | 90.2 | 89.42 |
| Apparent pH of formulations | 4.9 | 5.0 | 5.1 | 4.8 |
| % Yield for a 1 kg batch | 96.4% | 97.0% | 98.1% | 97.5% |

The compositions shown in Table 1, for a 1 Kg batch, are preferably prepared according to the following procedure.

Example of Manufacturing Procedure for a 1 Kg Batch

A. Disperse the Carbopol Ultrez polymer stepwise in ~80% (~800 gm) of the deionized water in a 1000 mL beaker. The EDTA should be dissolved here. Heat the water to a maximum of 50-55° C. to speed the dispersal of the Ultrez polymer. Discontinue heating when dispersion of the Ultrez is complete.

B. When the Ultrez polymer has fully dissolved pour it into a large stainless steel mixing bowl. Lock the stainless steel bowl into position on a mixer. Use the remaining weight of water to rinse the Ultrez-containing beaker into the mixing bowl.

C. Dissolve the Ketoprofen in the Transcutol P. Add this solution in small portions to the Ultrez, EDTA, and water mixture while stirring.

D. Add Paragon III and the fragrance after the above mixture cools to 40° C. or below while continuing to mix.

E. Neutralize with the Triethanolamine solution dropwise to a pH of 4.5 to 5.3 and continue mixing for 10 min, until uniform.

F. Record the pH and fill the product into labeled tubes or jars.

The method of delivery of the active ingredient(s) involves the application of the gel compositions to the skin over the desired site of action (e.g., the painful area) by inunction for a sufficient period of time to provide the desired local effect. All of the example compositions (and many other closely-related compositions) have been found to be aesthetically pleasing and to provide rapid relief of musculoskeletal pain. The repeated use of these compositions over many years has not resulted in any undesirable systemic side effects and did not produce any noticeable tissue damage, irritation, or sensitization. The compositions described here may be used for the topical delivery of a wide variety of therapeutic agents either alone or in combination, including both hydrophilic and hydrophobic moieties. In addition to ketoprofen, other preferred NSAIDs are diclofenac sodium, naproxen, ketorolac and piroxicam. Salts, esters, amides, prodrugs, and other derivatives of the NSAIDs may be used if they are suitable pharmacologically. For those NSAIDs that are chiral in nature the drug may be incorporated into the invention either as the racemate or an enantiomerically pure form.

The present invention has numerous unique features and advantages:

1. The invention contains 3-30% pharmaceutical grade DGME, preferably Transcutol P (preferably about 5.0%), which is not present in any of the NSAID-containing products currently on the market anywhere in the world.
2. The invention provides a rapid onset of effect as a result of the enhancement of the skin penetration of the NSAID by the DGME, preferably Transcutol P.
3. The invention provides a prolongation of the therapeutic effect due to the formation of intracutaneous depots containing the NSAID in the subcutaneous tissues as a result of the action of the DGME, preferably Transcutol P.
4. The invention contains no lower alcohols (typically ethanol, isopropanol, or mixtures thereof) which are volatile and can evaporate on the skin following application, or during storage in the container over time, or which can irritate the skin when applied topically and thus are unsuitable for applying directly to broken or damaged skin areas.
5. The "universal" nature of the carbomer polymers used in this invention (51) provides the properties desired over a diverse range of product types. Such properties include clarity, highly-efficient viscosity, non-tacky feel, rich buttery texture, and ease of preservation compared to many other "natural" thickening agents.
6. The easy dispersability of these newer carbomer polymers derivatives (the Ultrez series) speeds up significantly the overall manufacturing process by reducing greatly the wetting time and the tendency toward clumping observed with previous carbomer polymers.
7. The low viscosity of aqueous carbomer Ultrez polymer dispersions enables the following important processing and/or cost saving advantages:
   (i) Unlike the traditional carbomer polymers, it is possible to prepare very concentrated stock solutions with Carbopol® Ultrez polymers. When a Master batch is needed, a single batch at a concentration as high as 5% can be made more easily and more rapidly, saving valuable production time.

(ii) If the Master batch of unneutralized carbomer polymer stock dispersion needs to be pumped and transported along pipe lines within the production site, the low viscosity of Carbopol® Ultrez polymers dispersions makes this easier to accomplish.

(iii) Because of the low viscosity of concentrated Carbopol® Ultrez polymers stock dispersions, less foam is created during the initial stages of mixing due to less entrapment of air. Also, for the same reason, the subsequent mixing of additional ingredients is easy, reducing the processing time. The low dispersion viscosity at high concentrations of Carbopol® Ultrez polymer dispersions is primarily due to enhanced particle behavior of the resin. Carbopol® Ultrez polymer resin thickens systems primarily because of its higher rigidity rather than its swelling behavior. In traditional carbomer polymer dispersions the situation is exactly the reverse and hence the higher viscosities of their dispersions.

(iv) The unique balance between the swelling and the particle-like behavior in a Carbopol® Ultrez polymer makes it possible for a formulator to create everything from thin lotions to thicker creams using only a single rheology modifier. Current practice in the personal care industry is to use different carbomer polymers for lotions, creams and gels depending on the desired viscosity of the final product. The special properties of the Carbopol® Ultrez polymers result in additional performance benefits:

(i) Cost-Efficiency:

The dual nature of viscosity building by the Carbopol® Ultrez polymer, i.e., thickening by swelling at concentrations (c) close to its overlap concentration (c*)[1], and, thickening by its rigid particle nature at higher concentrations, leads to some interesting cost-efficiency considerations. It has been observed, for example, that certain personal care product formulations prepared with Carbopol® Ultrez polymers have 10, 20 or even 40% more viscosity than those prepared with traditional carbomer polymers, like Carbopol® 934, at the same polymer concentration. Conversely, a significantly lower concentration of Carbopol® Ultrez polymer in the formulation is required compared to traditional carbomer polymers to reach the same final viscosity.

[1] The overlap concentration (c*) represents an average segment concentration of individual polymer coils. Such concentration is determined by the mass of the macromolecule and the volume that it occupies in solution.

$$c^* = \frac{M/}{N_A * V_M}$$

where M is the molar mass of the particle, $V_M$ its volume and $N_A$ is Avogadro's number. Experimentally a marked change in behavior is observed when a certain concentration, c*, is exceeded. At c<c* the properties of individual macromolecules can be studied but at c>c* the individual macromolecules are no longer well separated from each other, and only an ensemble of many macromolecules is observed. The concentration c* is still very low ($\sim 10^{-2}$ g/ml) and the solution can certainly be considered "dilute". However, c* separates two dilute solution regimes of remarkably different behavior. To distinguish the moderately dilute solutions from the very dilute solutions the expression semidilute was coined to describe those that are moderately dilute. The concentration c* has a simple physical meaning. In dilute solution the coils are highly swollen, and the mean segmental concentration within a particle $c_{int}$ is rather low (<$10^{-2}$ g/mL). When the polymer concentration is increased, a stage is reached at which c=$c_{int}$=c*. At this point the segments of the coils start to overlap and become entangled. For this reason c* is called the overlap concentration. Of course, the over-all concentration can be increased beyond c* but this results in drastic changes in the solution properties. Reference: Aberle, T. and Burchard, W. (1997), Starches in Semidilute Aqueous Solution. Starch/Stärke, 49: 215-224. doi: 10.1002/star. 19970490602.

(ii) Less Tacky Feel:

Carbopol® Ultrez polymers swell significantly less than traditional carbomer polymers and their thixotropic index[2] is generally higher than those of traditional carbomer polymers. This unique combination of fundamental properties results in less tackiness of personal care products formulated with Carbopol® Ultrez polymers compared to products thickened with older, traditional carbomers. This improved, less tacky, feel has been observed consistently in formulations prepared in our laboratory using the four Carbopol® Ultrez carbomer polymers, i.e., Ultrez 10, 20, 21 and 30.

[2] The Carbopol polymer systems are shear-thinning or pseudoplastic in nature, i.e., their viscosity (a measure of resistance to flow) decreases as a shear stress is applied. An example of the application of a shear stress is as simple as shaking a bottle containing the polymer. A more sophisticated way to apply a shear stress is to use a flat round plate mounted horizontally on a vertical rod (spindle). The spindle is then placed into the material to be measured, and rotated at a defined speed for given time interval. This principle in used to measure viscosity in well-known devices such as the Brookfield viscometer. The Thixotropic Index is determined by measuring the viscosity of a sample at an initial (low) speed of rotation of the spindle (i.e., at a low applied shear stress) and then at a second (higher) speed of rotation (i.e., a higher applied shear stress). The second speed is typically 10 times the initial speed. A shear-thinning material will exhibit a lower viscosity as the applied shear stress (i.e., speed of rotation of the spindle) is increased. Thus for shear-thinning systems like the Carbopols the Thixotropic Index will be a numerical value greater than 1. This index therefore provides a relative measure of the material's ability to hold its shape.

Moreover, many of these features and advantages are unexpected, including:

1. DGME, preferably Transcutol P is able to dissolve a wide variety of nonpolar and hence poorly water-soluble drugs. The drug solution is then miscible with the polar water phase of the formulation. In addition, DGME, preferably Transcutol P is much less volatile than commonly used solvents such as ethanol and isopropanol and thus is much less likely to evaporate when the formulation is applied to the skin or when the product is stored in its container over several months of use. These unique properties of DGME, preferably Transcutol P as a formulation adjuvant simplify greatly the method of manufacture of the gel compared to, for example, an emulsion whose manufacture is much more technically demanding and labor intensive. In addition, the low solubility of NSAIDs in the oil phase of emulsions can lead to precipitation of drug during storage, resulting in a reduced efficacy and a shortened shelf life. DGME, preferably Transcutol P is able to dissolve a wide variety of hydrophobic materials (e.g., drugs) which remain miscible when mixed with the aqueous gel components and thus remain largely in solution and form an aesthetically pleasing gel.

2. The principles embodied in the invention provide a generally useful drug delivery platform that can be applied to the preparation of topical formulations for a wide variety of poorly water-soluble drugs including, but not limited to, antifungals, anti-infectives, steroids, retinoids, cytostatics, antivirals, etc.

3. The presence of the relatively non-volatile DGME, preferably Transcutol P (BP 196° C.) permits the amount of the more-volatile alcoholic cosolvent components, typically ethanol (BP 78.4° C.) or isopropanol (BP 82.5° C.), present in most of the commonly used similar gel preparations, to be reduced considerably or completely eliminated. This feature prevents the gel from drying out in its container or on the skin too rapidly such that a precipitate of some of the least soluble ingredients (e.g., the NSAID) is avoided. This is an important consideration since transcutaneous penetration of the drug from this unsightly layer of undissolved drug is very low or non-existent.

4. The addition of DGME, preferably Transcutol P permits the preparation of a non-greasy, non-staining gel devoid of any unpleasant odor. Any perceived odor will be slight and can be easily masked by the addition of a small amount of fragrance.

5. The addition of DGME, preferably Transcutol P enhances the penetration of the NSAID through the stratum corneum (barrier) layer of the skin into the subcutaneous tissues where the formation of intracutaneous depots of active ingredient can occur, a process known as Local Enhanced Topical Delivery or LETD. This provides for a rapid onset and a prolonged duration of the therapeutic effect.
6. Ketoprofen was proven to be chemically stable in the formulation for over 210 days at elevated temperature (40° C.) which indicates that a 2 year shelf life at room temperature (23° C.) is attainable.
7. The formulation is physically stable and no phase separation, syneresis, or significant drying out was observed in actual samples used by patients that were stored in large (1 lb.) jars at room temperature for more than 8 years. Obviously, the use of tubes with much smaller openings than the jars would provide for at least equal (likely greater) long-term stability during use by patients.
8. Many topical gels containing carbomer polymers are neutralized to a final pH of 6.5-7.0 to "achieve a maximum viscosity". If one examines carefully the pH vs. viscosity profiles of the carbomer polymers used here it is evident that a viscosity at or near the maximum is maintained from about pH 4.5 to 9. The present invention utilizes a pH in the preferred range 4.5 to 5.3 in order to retain a sufficiently high viscosity while also maximizing the fraction of ketoprofen in its unionized form. The unionized (non-polar) form of the drug is better able to partition out of the aqueous (polar) gel vehicle into and through the relatively non-polar stratum corneum more readily than the ionized form.

The composition of the present invention has numerous advantages and features, including:
1. The composition blends into the skin rapidly and provides relief of inflammation and pain in rheumatoid arthritis, osteoarthritis, soft tissue injuries, strain, sprain and sports injuries.
2. The composition is safe and effective.
3. The composition uses a relatively small number of commonly used and safe components and is easy to manufacture.
4. The composition provides a consistently high yield of finished product, typically >95% for 1 Kg batches.
5. The composition is relatively inexpensive to manufacture, as a result of factors 3 and 4 listed above.
6. The composition can be applied for an extended period, e.g., 10-12 days, without any significant risk of harmful effects.
7. The composition provides an increased duration of therapeutic effect due to the formation of intracutaneous depots in the skin containing the active ingredient(s).
8. The composition is pharmaceutically elegant, i.e., it is aesthetically pleasing to the touch, has no runny consistency or greasy feel, and has no undesirable odor.
9. The composition is easily removed from skin or clothing by washing with water.
10. The composition does not stain clothing.
11. The composition does not cause irritation, dryness, or other undesirable changes to the skin.
12. The composition is more physically stable than an emulsion and eliminates the possibility of any creaming or cracking that can occur with emulsions.
13. The composition avoids the need for a surfactant which is essential when preparing an emulsion formulation. This is advantageous as surfactants often cause skin irritation, especially on broken skin surfaces.
14. The lower blood levels of NSAID following topical application of the composition of the present invention compared to those observed following oral dosing (typically 5% or less) results in a relatively low potential for the patient to experience the gastrointestinal, cardiovascular, or renal toxicities that can be observed following oral dosing.
15. The composition allows the active ingredient (drug) contained therein to avoid significant metabolism in the gut or by the liver (the so-called "first-pass" effect) because the drug does not pass through gut or the liver before exerting its therapeutic effect.
16. The lower blood levels of NSAID following topical application of the composition of the present invention compared to those observed following oral dosing results in a relatively low potential for drug interactions with other therapeutic agents being used by the patient.

Various changes may be made to the foregoing invention without departing from the spirit and scope thereof.

REFERENCES CITED

1. Gavura, S., Anti-inflammatory drugs: A closer look at the risks, Science-Based Medicine, Mar. 15, 2013.
2. Meek, I. L., van de Laar, M. A. F. J. and Vonkeman, H. E., Non-steroidal anti-inflammatory drugs: An overview of cardiovascular risks, Pharmaceuticals, 3: 2146-2162 (2010).
3. Bystrianyk, R., More hospitalized from NSAID bleeding than all American war casualties, Health Sentinel, 16: 00 (Jan. 10, 2010).
4. Merck Announces Voluntary Worldwide Withdrawal of VIOXX®, Merck and Co., Inc., Whitehouse Station, N.J., Sep. 30, 2004.
5. Smith, A., Pfizer pulls Bextra off the market, CNN Money, Apr. 7, 2005. http://money.cnn.com/2005/04/07/news/fortune500/bextra/
6. McGettigan P, Henry D., Use of non-steroidal anti-inflammatory drugs that elevate cardiovascular risk: an examination of sales and essential medicines lists in low-, middle-, and high-income countries, PLOS Med. 10 (2): Feb. 12, 2013. e1001388.doi:10.1371/journal.pmed.1001388
7. Knox, R., World's most popular painkiller raises heart attack risk, NPR, Feb. 12, 2013. http://www.npr.org/blogs/health/2013/02/12/171832741/
8. Reddy, K. S., Roy, A., Cardiovascular Risk of NSAIDs: Time to Translate Knowledge into Practice. PLOS Med 10(2): Feb. 12, 2013. e1001389. doi:10.1371/journal.pmed.1001389
9. Shah, V. P., Behl, C. R., Flynn, G. L., Higuchi, W. I., Schaefer, H., Principles and criteria in the development and optimization of topical therapeutic products, Int. J. Pharmaceut. 82: 21-28 (1992).
10. Shah, V. P., Behl, C. R., Flynn, G. L., Higuchi, W. I., Schaefer, H., Principles and criteria in the development and optimization of topical therapeutic products, Pharm. Res. 9: 1107-1111 (1992).
11. Shah, V. P., Behl, C. R., Flynn, G. L., Higuchi, W. I., Schaefer, H., Principles and criteria in the development and optimization of topical therapeutic products. J Pharm Sci. 81: 1051-1054 (1992).
12. Moore, R. A., Tramer, M. R., Carroll, D., Wiffen, P. J., McQuay, H. J. Quantitative systematic review of topically applied non-steroidal anti-inflammatory drugs, BMJ 316: 333-338 (1998).
13. Grahame, R. Transdermal non-steroidal anti-inflammatory agents, Brit. J. Clin. Pract. 49: 33-35 (1995).

14. McNeill, S. C., Potts, R. O., Francoeur, M. L. Locally enhanced topical delivery (LETD) of drugs: does it truly exist? Pharm. Res. 9: 1422-1427 (1992).
15. Singh, P., Roberts, M. S., Skin permeability and local tissue concentrations of non-steroidal anti-inflammatory drugs after topical application, J. Pharmacol. Exp. Ther. 268: 144-151 (1994).
16. Ballerini, R., Casini, A., Chinol, M., Mannucci, C., Giaccai, L., Salvi, M., Study on the absorption of ketoprofen topically administered in maw comparison between tissue and plasma levels, Int. J. Clin. Pharm. Res. VI: 69-72 (1986).
17. Flouvat, B., Roux, A., Delhotel-Landes, B., Pharmacokinetics of ketoprofen in man after repeated percutaneous administration, Arzneim. Forsch. 39: 812-815 (1989).
18. Hadgraft, J., du Plessis, J., Goosen, C., The selection of non-steroidal anti-inflammatory agents for dermal delivery. Int. J. Pharmaceut. 207: 31-37 (2000).
19. Cordero, J. A., Alarcon, L., Escribano, E., Obach, R., Domenech, J., A comparative study of the transdermal penetration of a series of nonsteroidal anti-inflammatory drugs, J. Pharm. Sci. 86: 503-507 (1997).
20. Dreiser, R. L., Topical antirheumatic drug therapy: current practice and future trends. Eur. J. Rheumatol. Inflamm. 14: 3-8 (1994).
21. Panchagnula, R. and Ritschel, W. A., Development and evaluation of intracutaneous depot formulation of corticosteroids using Transcutol as a cosolvent: in vitro, ex-vivo and in vivo rat studies. J. Pharm. Pharmacol. 43: 609-614 (1991).
22. Ritschel, W. A. and Hussain, A. S., In vitro skin penetration of griseofulvin in rat and human skin from an ointment dosage form. Arzneim. Forsch./Drug Res. 38: 1630-1632 (1988).
23. Yazdanian, M. and Chen, E., The effect of diethylene glycol monoethyl ether as a vehicle for topical delivery of ivermectin. Vet. Res. Commun. 19: 309-319 (1995).
24. Altman, R. D., Barthel, H. R., Topical therapies for osteoarthritis, Drugs 71:1259-1279 (2011).
25. Wiegand, T. J. and Tarabar, A., Nonsteroidal anti-inflammatory agent toxicity, Medscape, Nov. 14, 2012. http://emedicine.medscape.com/article/816117
26. Lawrence, R. C., Felson, D. T., Helmick, C. G., Arnold, L. M., Choi, H., Dew, R. A., Gabriel, S., Hirsch, R., Hochberg, M. C., Hunder, G. G., Jordan J. M., Katz, J. N., Kremers, H. M. and Wolfe, F., Estimates of the prevalence of arthritis and other rheumatic conditions in the United States. Part II. Arthritis Rheum. 58(1):26-35 (2008). doi: 10.1002/art.23176.
27. Anon, The pain management market outlook to 2016, Business Insights, 2011). http://www.futuramedical.com/content/products/pain_relief.asp
28. Anon, Easing joint pain: Are NSAIDs right for you? Consumer Reports (2013) http://www.consumerreports.org/health/resources/pdf/best-buy-drugs/2pager_NSAIDs.pdf
29. Beetge, E., du Plessis, J, Müller, D. G., Goosen, C., van Rensburg, F. J., The influence of the physicochemical characteristics and pharmacokinetic properties of selected NSAID's on their transdermal absorption. Int. J. Pharmaceut. 193: 261-264 (2000).
30. Cordero, J. A., Camacho, M., Obach, R., Domenech, J., Vila, L., In vitro index of topical anti-inflammatory activity to compare a series of NSAIDs. Eur. J. Pharm. Biopharm. 51: 135-142 (2001).
31. Meloun M, Bordovska S, Galla L. The thermodynamic dissociation constants of four non-steroidal anti-inflammatory drugs by the least-squares nonlinear regression of multiwavelength spectrophotometric pH-titration data. J. Pharm. Biomed. Anal. 45: 552-564 (2007).
32. Péhourcq, F., Matoga, M., Jarry, C., Bannwarth, B., Study of the lipophilicity of arylpropionic non-steroidal anti-inflammatory drugs. A comparison between LC retention data on a polymer-based column and octanol-water partition coefficients, J. Liq. Chrom. & Rel. Technol. 24: 2177-2186 (2001).
33. Airaksinen, O., Venalainen, J., Piletilainen, T., Ketoprofen 2.5% gel versus placebo gel in the treatment of acute soft tissue injuries. Int. J. Clin. Pharm. Therapy and Tox. 31: 561-563 (1993).
34. Harris, R. H. and Vavra, I., "Ketoprofen", Anti-Inflammatory and Anti-Rheumatic Drugs, Vol II. (Ed., Rainsford, K. D.), CRC Press, Inc., Boca Raton, Fla. (1985).
35. Patel, R. K., Leswell, P. F., Comparison of ketoprofen, piroxicam, and diclofenac gels in the treatment of acute soft-tissue injury in general practice. Clin. Ther. 18: 497-507 (1996).
36. Massey, T., Derry, S., Moore, R. A. and McQuay, H. J., Topical NSAIDs for acute pain in adults, Cochrane Database Syst. Rev. 2010 Jun 16;(6):CD007402. doi: 10.1002/14651858.CD007402.pub2.
37. Mason, L., Moore, R. A., Derry, S. and McQuay, H. J., Topical NSAIDs for acute pain: a meta-analysis, BMC Family Practice 5:10 (2004). doi:10.1186/1471-2296-5-10; This article can be found online at: http://www.biomedcentral.com/1471-2296/5/10
38. Anon, Clinical knowledge summary for sprains and strains, National Institute for Health and Care Excellence (NICE), October (2012).
39. Coaccioli, S., Ketoprofen 2.5% gel: a clinical overview, Eur. Rev. Med. Pharmacol. Sci. 15: 943-949 (2011).
40. Sarzi-Puttini P, Atzeni F, Lanata L, Bagnasco M., Efficacy of ketoprofen vs. ibuprofen and diclofenac: a systematic review of the literature and meta-analysis, Clin. Exp. Rheumatol., 31(5):731-738 (2013). Epub 2013 May 17.
41. Ritschel, W. A., Panchagnula, R., Stemmer, K., Ashraf, M., Development of an intracutaneous depot for drugs. Skin Pharmacol. 4: 235-245 (1991).
42. Touitou, E., Levi-Schaffer, F., Shaco-Ezra, N., Ben-Yossef, R., Fabin, B., Enhanced permeation of theophylline through the skin and its effect on fibroblast proliferation. Int. J. Pharm. 70: 159-166 (1991).
43. Fabin, B., and Touitou, E., Localization of lipophilic molecules penetrating rat skin in vivo by quantitative autoradiography. Int. J. Pharm. 74: 59-65 (1991).
44. Harrison, J. E., Watkinson, A. C., Green, D. M., Hadgraft, J., Brain, K., The relative effect of Azone® and Transcutol® on permeant diffusivity and solubility in human stratum corneum. Pharm. Res. 13: 542-546 (1996).
45. Ritschel, W. A. and Hussain, A. S., Influence of selected solvents on penetration of griseofulvin in rat skin, in vitro. Pharm. Ind. 50: 483-486 (1988).
46. Panchagnula, R., Development of an intracutaneous depot for drugs, Ph.D. Dissertation, University of Cincinnati (1991).
47. Gürol, Z., Hekimoğlu, S., Demirdamar, R., Sumnu, M. Percutaneous absorption of ketoprofen. I. In vitro release and percutaneous absorption of ketoprofen from different ointment bases. Pharm. Acta Hely. 71: 205-212 (1996).
48. Desai, D. D., Hasman, D. F., Schmucker-Castner, J. F., Advances in Carbomer polymer technology, BF Goodrich, Specialty Chemicals, Cleveland, Ohio 44141.

49. Anon, Carbopol® Ultrez 10 polymer for personal care applications, TDS-225, Lubrizol Advanced Materials, Inc., Cleveland, Ohio 44141, January 2002.
50. Barkin, R. L., Topical nonsteroidal anti-inflammatory drugs: The importance of drug, delivery, and therapeutic outcome, Amer. J. Ther. Feb. 22 (2012).
51. Anon, Carbopol® Ultrez™, The Polymer as Universal as Water, BF Goodrich Company, Specialty Chemicals, 9921 Brecksville Road, Cleveland, Ohio 44141-3247.

What is claimed is:

1. A composition for topical application onto the skin comprising at least one NSAID, a penetration enhancer, an alcohol-free aqueous based carrier, and a gelling agent, a thickening agent or a rheology modifier, wherein the NSAID is selected from Ketoprofen, alone, or in combination with, one or more additional NSAIDs selected from the group consisting of flurbiprofen, ibuprofen, naproxen, fenoprofen, pirprofen, carprofen, oxaprozin, tiaprofenic acid, acetylsalicylic acid, diclofenac, diflunisal, etodolac, flufenamic acid, indomethacin, ketorolac, meclofenamate, mefenamic acid, nabumetone, oxyphenbutazone, phenylbutazone, piroxicam, meloxicam, salsalate, sodium salicylate, sulindac, tenoxicam, tolmetin and celecoxib.

2. The composition of claim 1, wherein the NSAID is Ketoprofen, the penetration enhancer comprises DGME, and the gelling agent, thickening agent or rheology modifier comprises a carbomer polymer.

3. The composition of claim 2 comprising:
Ingredients % (w/w)
NSAID 1.0-15.0
Penetration Enhancer 3.0-30.0
Gelling Agent, Thickening Agent or Rheology Modifier 0.5-2.0
Water Balance.

4. The composition of claim 3, comprising about 5% (w/w) of said penetration enhancer.

5. The composition of claim 2, further including one or more of a neutralizing agent, a chelating agent, a fragrance, a preservative, and a coloring agent.

6. The composition of claim 5, comprising:
Ingredients % (w/w)
Ketoprofen 1.0-15.0
DGME 3.0-30.0
Carbomer polymer 0.5-2.0
Triethanolamine 0.2-1.5
Disodium EDTA Dihydrate 0.04-0.10
Preservative 0.4-1.0
Fragrance 0.2-0.5
Deionized water 30.0-95.0.

7. The composition according to claim 5, wherein the neutralizing agent is selected from the group consisting of Tromethamine, Triethanolamine, aminomethyl propanol, tetrahydroxypropylethylenediamine, sodium hydroxide and potassium hydroxide.

8. The composition according to claim 5, adjusted to a pH in the range 4.5 to 5.3.

9. The composition according to claim 5, wherein the preservative is selected from the group consisting of DMDM Hydantoin, Germall Plus, Germaben II, methyl-, ethyl-, propyl-, and butyl- paraben, Euxyl K400, Bronopol, sodium benzoate, chlorhexidine, benzalkonium chloride, 2-phenoxyethanol, cetrimide, potassium sorbate, Paragon, and Paragon III.

10. The composition according to claim 1, further comprising a smooth muscle relaxant.

11. The composition of claim 10, wherein the smooth muscle relaxant comprises cyclobenzaprine or dantrolene.

12. The composition according to claim 1, further comprising an agent which can increase the blood flow to the site of administration.

13. The composition according to claim 12, wherein the agent is selected from the group consisting of capsaicin, mustard oil, menthol, methyl salicylate, verapamil, diltiazem, and alprostidil.

14. The composition according to claim 1, further comprising one or more additional active agents, selected from the group consisting of an antihistamine, a corticosteroid, a local anesthetic agent, a topical analgesic and an antibiotic.

15. The composition according to claim 14, wherein the antihistamine is selected from the group consisting of diphenhydramine hydrochloride and chlorpheniramine maleate; the corticosteroid is selected from the group consisting of hydrocortisone, dexamethasone, flumethasone, prednisolone, methylprednisolone, clobetasol propionate, betamethasone benzoate, betamethasone dipropionate, diflorasone diacetate, fluocinonide, mometasone furoate, and triamcinolone acetonide, the local anesthetic agent is selected from the group consisting of benzocaine, lidocaine, prilocalne and dibucaine; and the topical analgesic is selected from the group consisting of glycol salicylate, methyl salicylate, 1-menthol, d,1-camphor and capsaicin.

16. The composition according to claim 15, wherein the hydrocortisone is selected from the group consisting of hydrocortisone, a hydrocortisone-21-monoester, and a hydrocortisone-17,21-diester.

17. The composition according to claim 16, wherein the hydrocortisone-21-monoester is selected from the group consisting of hydrocortisone-21-acetate, hydrocortisone-21-butyrate, hydrocortisone-21-propionate and hydrocortisone-21-valerate and the hydrocortisone-17,21-diester is selected from the group consisting of hydrocortisone-17,21-diacetate, hydrocortisone-17-acetate-21-butyrate and hydrocortisone-17,21-dibutyrate.

18. The composition according to claim 1, further comprising one or more additional agents selected from the group consisting of benzocaine, tetracaine, mepivacaine, prilocalne, bupivacaine, lidocaine; acetaminophen, naproxen, ibuprofen, flurbiprofen, diclofenac, and salicylamide; an amebicide, abroad or medium spectrum antibiotic, an antifungal medication, penicillin, cephalosporin, a steroid, ACTH, an anabolic steroid, an androgenic steroid, a corticosteroid, glucocorticoid, gonadotropin, a gonadotropin-releasing human growth hormone, progesterone, progestogen, and progestogen and estrogen in combination.

* * * * *

UNITED STATES PATENT AND TRADEMARK OFFICE
CERTIFICATE OF CORRECTION

Page 1 of 1

PATENT NO.           : 9,012,402 B1
APPLICATION NO.      : 14/302164
DATED                : April 21, 2015
INVENTOR(S)          : Blanchard It is certified that error appears in the above-identified patent and that said Letters Patent is hereby corrected as shown below:

In the specification

Col. 21, line 10 "in maw comparison" should read --in man comparison--

Signed and Sealed this
Twenty-second Day of December, 2015

Michelle K. Lee
*Director of the United States Patent and Trademark Office*